US012677935B2

(12) United States Patent
Mastrianna et al.

(10) Patent No.: US 12,677,935 B2
(45) Date of Patent: Jul. 14, 2026

(54) SCALP TREATMENT APPLICATOR FOR APPLYING SCALP TREATMENT COMPOSITIONS

(71) Applicants: Gina Marie Mastrianna, Westerly, RI (US); Eugene Mastrianna, Northfield, CT (US)

(72) Inventors: Gina Marie Mastrianna, Westerly, RI (US); Eugene Mastrianna, Northfield, CT (US)

( * ) Notice: Subject to any disclaimer, the term of this patent is extended or adjusted under 35 U.S.C. 154(b) by 4 days.

(21) Appl. No.: 18/617,488

(22) Filed: Mar. 26, 2024

(65) Prior Publication Data

US 2024/0341445 A1 Oct. 17, 2024

Related U.S. Application Data

(60) Provisional application No. 63/454,694, filed on Mar. 26, 2023.

(51) Int. Cl.
| | |
|---|---|
| *A46B 11/00* | (2006.01) |
| *A45D 24/26* | (2006.01) |
| *A61M 35/00* | (2006.01) |

(52) U.S. Cl.
CPC .......... *A46B 11/0041* (2013.01); *A45D 24/26* (2013.01); *A61M 35/003* (2013.01)

(58) Field of Classification Search
CPC .......... A46B 11/0041; A46B 2200/104; A46B 11/0062; A46B 17/04; A46B 11/00; A46B 11/002; A46B 2200/102; A46B 2200/1033; A46B 2200/20; A46B 9/005; A45D 24/26; A45D 24/22; A45D 34/045; A45D 2200/054; A61M 35/003
See application file for complete search history.

(56) References Cited

U.S. PATENT DOCUMENTS

| | | | | |
|---|---|---|---|---|
| 4,543,913 | A | * | 10/1985 | Wilkeson ............. A01K 13/003 |
| | | | | 401/28 |
| 9,706,832 | B2 | * | 7/2017 | Price .................... A46B 5/0075 |
| 11,324,302 | B1 | * | 5/2022 | Heilman ............ A46B 11/0041 |
| 2007/0201941 | A1 | * | 8/2007 | Koptis .................. B65D 51/32 |
| | | | | 401/269 |
| 2011/0049081 | A1 | * | 3/2011 | Bourguignon ......... B65D 51/28 |
| | | | | 215/227 |
| 2021/0127823 | A1 | * | 5/2021 | Gaither ............. A46B 11/0065 |

FOREIGN PATENT DOCUMENTS

WO WO-2020201585 A1 * 10/2020

* cited by examiner

*Primary Examiner* — Rebecca E Eisenberg
*Assistant Examiner* — Gabriella E Burnette
(74) *Attorney, Agent, or Firm* — Feeney IP Law; Daniel W. Sullivan; Alan F. Feeney

(57) ABSTRACT

A scalp treatment device is provided. More particularly, the present invention relates to scalp treatment applicators and methods of applying a scalp treatment composition to the scalp of a user. The scalp treatment applicator can be used to apply hair oils and serums to the scalp. The upper handle of the applicator is preferably made of a plastic material so that the handle can be squeezed to dispense the scalp treatment composition. The upper handle is preferably conical-shaped, and the applicator can include a lower cap. The applicator preferably has a unique tear-shape appearance when the lower cap is fastened to the upper handle.

8 Claims, 6 Drawing Sheets

24

27

24

SCALP TREATMENT APPLICATOR FOR APPLYING SCALP TREATMENT COMPOSITIONS

CROSS-REFERENCE TO RELATED APPLICATIONS

The application claims the benefit of U.S. Provisional Patent Application No. 63/454,694 filed Mar. 26, 2023, the entire disclosure of which is hereby incorporated by reference.

BACKGROUND OF THE INVENTION

Field of the Invention

The present invention relates generally to a scalp treatment device. More particularly, the present invention relates to scalp treatment applicators and methods of applying a scalp treatment composition to the scalp of a user. The scalp treatment applicator can be used to apply hair oils and serums to the scalp.

Brief Review of the Related Art

There are numerous hair and scalp treatment products in the marketplace today. In general, hair oils are primarily made of natural oils and help to nourish, strengthen, and support hair and scalp health. Hair oils normally are absorbed by the hair and scalp. Hair serums are commonly made of silicone-based ingredients and normally coat or seal the hair. Hair serums generally provide a protective layer over the individual hair strands. Hair serums help give the hair a shiny appearance. These hair serums also can provide protection again environmental elements and help control hair frizz.

Many consumers will use hair oils on their scalp to try to stimulate hair growth. These oil-based products typically contain carrier oils and essential oils. For example, formulations containing such carrier oils as olive, avocado, almond, coconut, grapeseed, and argan oils can be used. Essential oils contain chemical compounds from plants and include, for example, peppermint, tea tree, rosemary, lavender, lemongrass, and bergamot oils. Also, keratin growth factor hair serums may help promote hair growth, shine, and control.

Other hair and scalp treatment products include, for example, shampoos, conditioners, hair coloring formulations, hair bleach, and hair gels. Although some conventional applicator devices can be generally effective for applying hair and scalp treatment products, they can have some drawbacks. For example, some conventional applicators do not uniformly apply hair and scalp treatment products. This non-uniform application can lead to globs and clumps forming in the hair. Some conventional applicators are not easy to use, and this causes the user to get his/her hands messy with the oils and serums. Also, such applicators may be relatively cumbersome and difficult to carry in a purse or handbag. Thus, there is a need for a new scalp treatment applicator that is easy to use, consumer-friendly, and will evenly distribute the hair/scalp oil onto the hair and scalp. The present invention provides such a scalp treatment applicator. Other advantages and benefits of the present invention are described further below.

SUMMARY OF THE INVENTION

The present invention provides a scalp treatment applicator for applying a scalp treatment composition to the scalp of a user. In one preferred embodiment, the applicator comprises: a) an upper handle having upper and lower portions, wherein the upper and lower portions define a hollow cavity, the lower portion being adapted for receiving a main body member; b) a main body member, the main body member being attached to the upper handle, the main body member comprising a head member, insert member, and base member, the insert member being disposed between the head member and base member, and the base member being removably coupled to the head member; c) multiple teeth extending downwardly from the base member, at least one tooth having a neck containing a channel that extends from a top opening, through the neck of the tooth, and terminates at a bottom opening of the tooth, from which the composition is dispensed; and d) a removable lower cap for enclosing the main body member, the lower cap being removably fastened to the upper main body member.

In one embodiment, the upper handle is made of a plastic material so that the handle can be squeezed to dispense the scalp treatment composition. The upper handle is preferably conical-shaped. The head member can be fastened to the upper handle in any suitable way. For example, the head member can be integrally molded to the upper handle or snap-fitted to the upper handle.

The head member of the applicator can have a threaded inner surface and the base member has a threaded outer surface so that the base member can be screwed into the head member. In another example, the head member of the applicator has a threaded outer surface, and the lower cap has a threaded inner surface so that the cap can be screwed onto the head member.

The insert divider of the applicator preferably contains an extended tab. In one example, the insert divider contains divider members that define slits for dispensing the scalp treatment composition. The present invention also encompasses methods of applying a scalp treatment composition to the scalp of a user.

BRIEF DESCRIPTION OF THE DRAWINGS

The novel features that are characteristic of the present invention are set forth in the appended claims. However, the preferred embodiments of the invention, together with further objects and attendant advantages, are best understood by reference to the following detailed description in connection with the accompanying drawings in which:

DETAILED DESCRIPTION OF THE INVENTION

Figure 1:
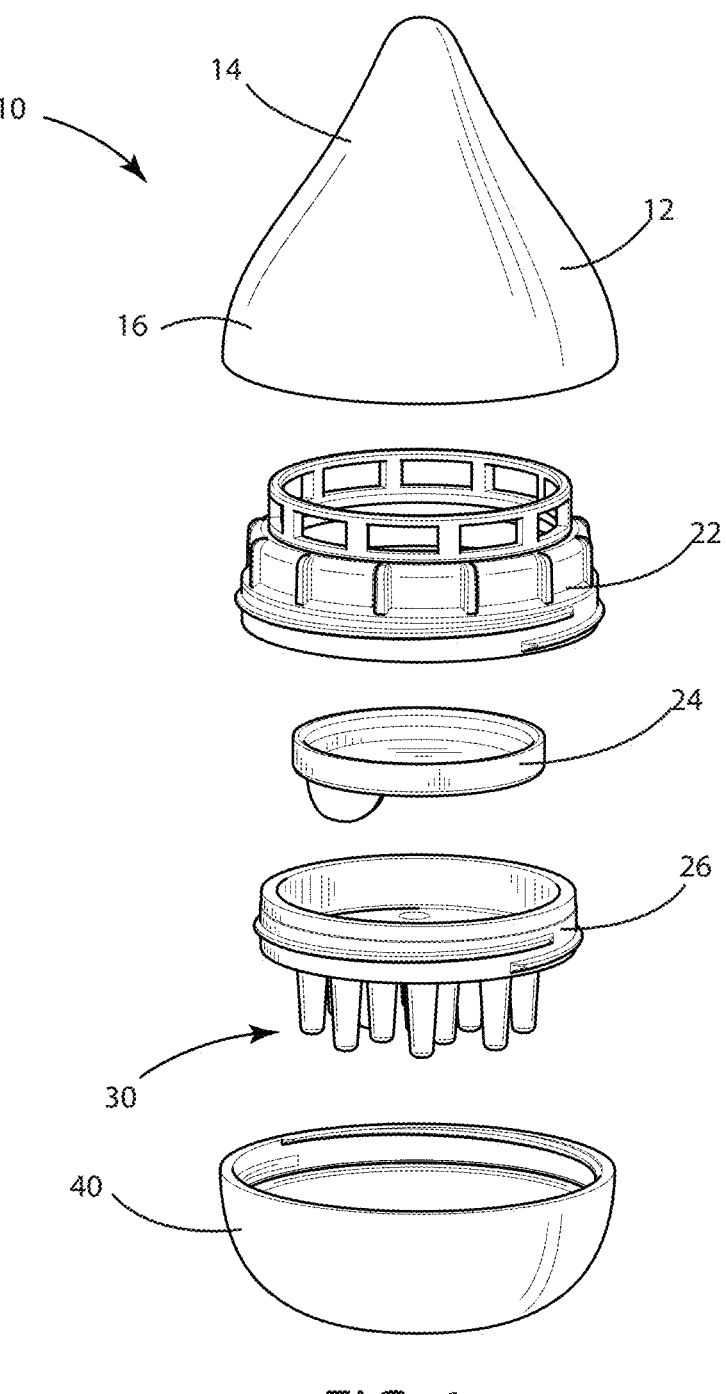
FIG. 1 is an exploded view of one embodiment of the scalp treatment applicator of the present invention.
Figure 2:
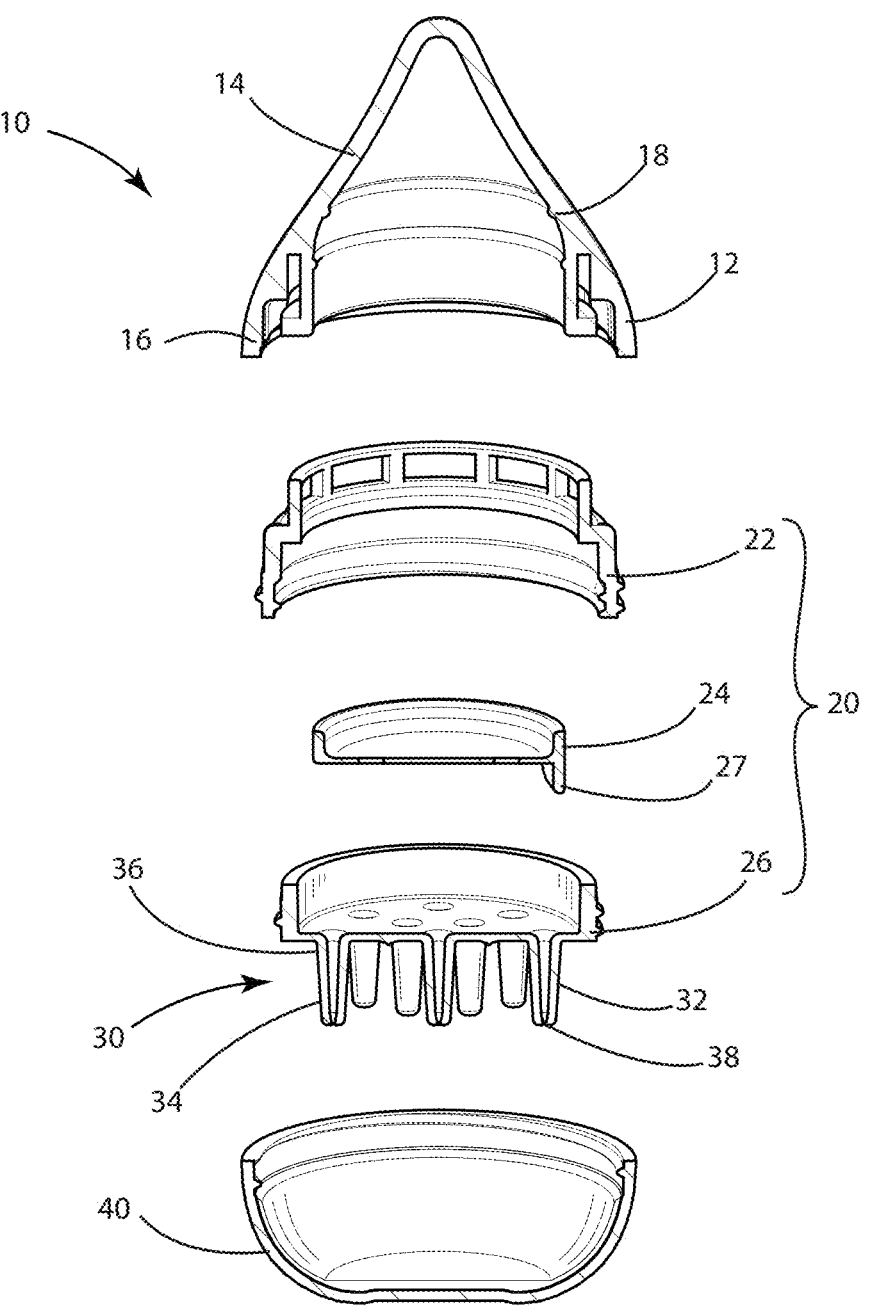
FIG. 2 is cross-sectional view of the scalp treatment applicator shown in FIG. 1.

Referring to the Figures, where like reference numerals are used to designate like elements, FIGS. 1 and 2 show one embodiment of the scalp treatment applicator (10) of the present invention. The applicator includes: a) an upper handle (12) having upper (14) and lower (16) portions, wherein the upper and lower portions define a hollow cavity (18), the lower portion (16) being adapted for receiving a main body member (20); b) a main body member (20), the main body member being attached to the upper handle (12), the main body member (20) comprising a head member (22), insert divider member (24), and base member (26), the insert member (24) being disposed between the head member (22) and base member (26), and the base member being removably coupled to the head member; c) multiple teeth (30) extending downwardly from the base member (26), at least one tooth having a neck (32) containing a channel (34) that extends from a top opening (36), through the neck (32) of the tooth, and terminates at a bottom opening (38) of the tooth, from which the scalp treatment composition is dispensed; and d) a removable lower cap (40) for enclosing the main body member (20), the lower cap (40) being removably fastened to the head member (22) of the main body member (20).

As shown in FIGS. 1 and 2, the upper handle (12) is preferably conical-shaped so that a user can easily grasp the handle with their left or right and squeeze the handle while passing the applicator (10) along the user's scalp as discussed in further detail below. The upper handle (12) is preferably made of a relatively soft thermoplastic material so that it can be squeezed easily. The upper handle (12) is ergonomically designed so that user can comfortably and efficiently use the applicator to apply the scalp treatment composition. By the term, "scalp treatment composition," it is meant any formulation that can be applied to the hair or scalp including, but not limited to, hair oils and serums, medications, shampoos, conditioners, hair coloring formulations, hair bleach, hair gels, and the like.

Figure 3:
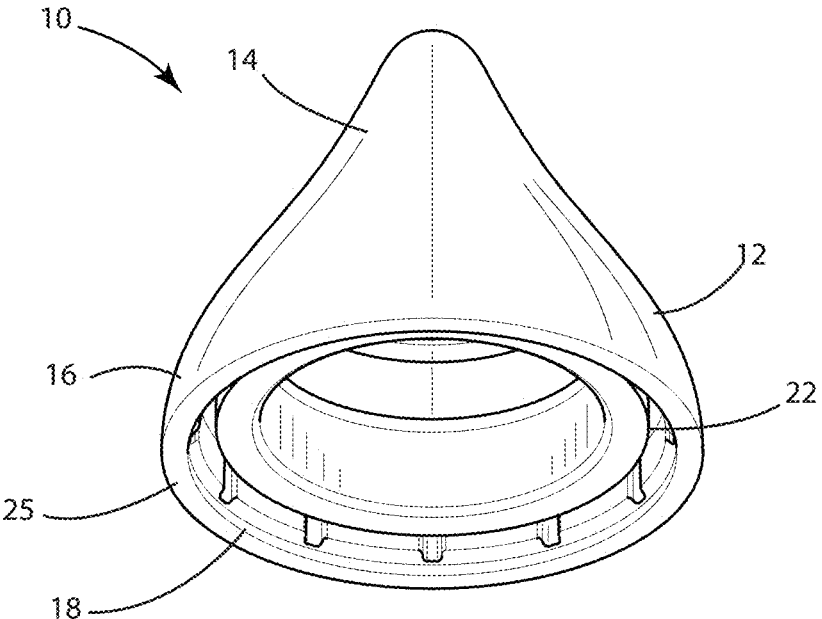
FIG. 3 is perspective view of one embodiment of the upper handle and head member components, wherein the upper handle and head member are shown as an integral unit.

The upper handle (12) has upper (14) and lower (16) portions that define a hollow cavity (18). The lower portion (16) is adapted for receiving a main body member (20). The main body member (20) can be attached to the upper handle (12). More particularly, the main body member (20) comprises a head member (22), intermediate insert divider member (24), and base member (26). The head member (22) can be fastened to the upper handle (12) in any suitable manner. Referring to FIG. 3, in one embodiment, the head member (22) is integrally molded with the upper handle (12). In another embodiment, the head member (22) is snap-fitted to the upper handle (12). In yet another embodiment, the head member (22) can be threaded onto the upper handle (12).

In FIG. 3, the top rim portion (25) of the head member (22) is shown protruding from the lower portion (16) of the upper handle (12). In one preferred embodiment the inner periphery of the top rim portion (25) is threaded so that the head member (22) can be joined to the base member (26) as discussed further below. In addition, in one preferred embodiment, the outer periphery of the upper rim portion (25) is threaded so that it can be joined to the lower cap (40) also as discussed further below.

Referring back to FIGS. 1 and 2, the intermediate insert divider member (24) is disposed between the upper head member (22) and lower base member (26). The insert divider (24) further contains divider members that define slits (not shown) for dispensing the scalp treatment composition. The insert divider (24) fits within the head member (22) such the slits will only open and allow the treatment composition to be dispensed when pressure is applied to the upper handle (12). The slits also prevent leaking of the liquid when the device (10) is not being used. The base member (26) is removably coupled to the head member (22). For example, the outer periphery of the base member (26) can contain screw threads that will engage screw threads placed along the inner periphery of the head member (22). The threaded structure will allow the base member (26) to be screwed into the head member (22).

Figure 4:
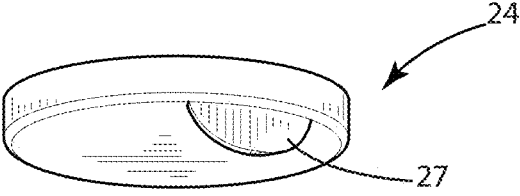
FIG. 4 is a side view of one embodiment of the insert divider component showing the extended tab on the lower surface.
Figure 5:
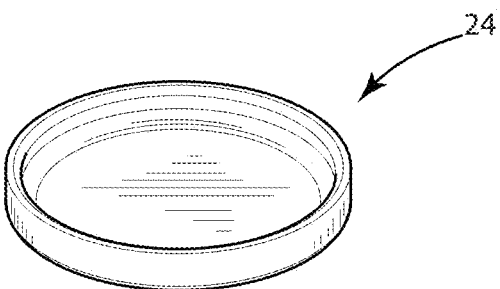
FIG. 5 is a top view of one embodiment of the insert divider component.

As discussed above, the insert divider member (24) is disposed between the head member (22) and base member (26). The insert divider (24) contains divider members that define slits for dispensing the scalp treatment composition. The insert divider (24) fits within the head member (22) such the slits will only open and allow the treatment composition to be dispensed when pressure is applied to the upper handle (12). The scalp treatment composition is applied from the upper handle (12) and through the main body member (20) as discussed further below. As shown in FIGS. 4 and 4A, the upper surface of the insert divider (24) can be flat, and the lower surface of the insert divider can include a tab (27). A user can easily pinch the tab (27) with their fingers and remove the insert divider (24) from the applicator (10) when needed.

Figure 6:
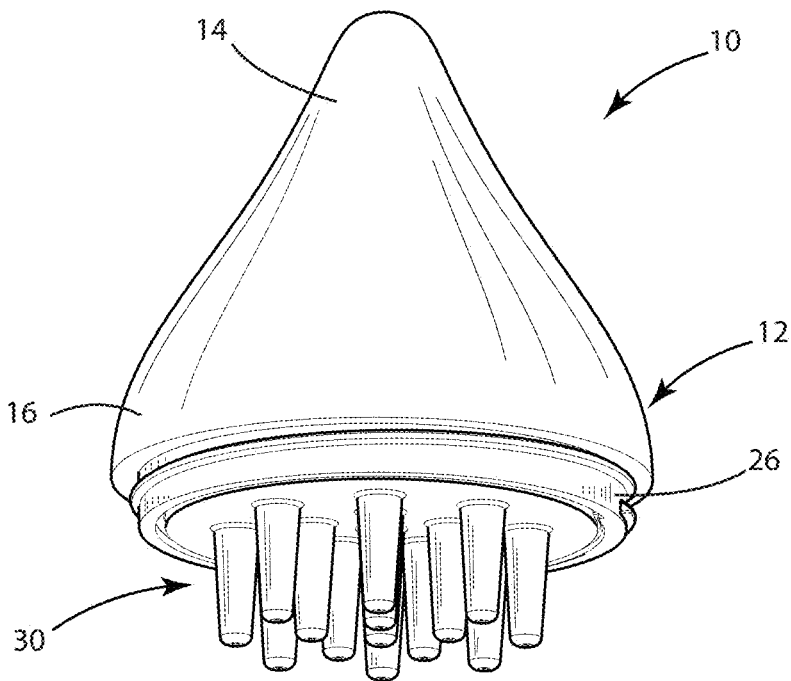
FIG. 6 is a perspective view of one embodiment of the scalp treatment applicator of the present invention showing the teeth extending downwardly from the base member.

Turning to FIG. 6, in practice, the base member (26) can be unscrewed from the head member (22) of the main body member (20) and then the user can fill the applicator with the scalp treatment composition. The user can then screw the base member (26) back onto the head member (22) of the main body member (20), and the applicator (10) is ready to be used. As discussed above, the upper handle (12) retains the scalp treatment composition until the user is ready to apply it. In one preferred embodiment, the upper handle (12) holds about two (2) ounces of liquid.

When ready, the user can squeeze the upper handle (12) and dispense the scalp treatment composition. The user can control the amount of scalp treatment composition that is dispensed by adjusting the pressure applied to the upper handle (12). That is, the user can squeeze the upper handle (12) lightly or heavily, and this difference in squeezing pressure will change how much scalp treatment composition is dispensed.

The liquid is dispensed through the teeth (30) located in the bottom region of the applicator device. As shown in FIGS. 1, 2 and 6, the teeth (30) have necks (32) containing passages or channels (34) that extend from a top opening (36), through the neck of the teeth, and terminate at a bottom opening (38) from which the composition is dispensed. The teeth (30) can have any suitable shape including, but not limited to, rectangular, square, and triangular shapes. In one preferred embodiment, the teeth (30) are rectangular shaped. The rectangular-like shaped teeth have a base affixed to the base member (26) of the main body member (20). The base member (26) surface can have any suitable geometry. For example, the base surface can have a rectangular, square, oval, or other shaped cross-section.

As discussed above, the base surface of the tooth has a bottom opening (38) so that when the tooth base is affixed to the base member of the main body member, a top opening (36) is present that allows the composition to flow into a channel (34) extending through the longitudinal neck (32) of the tooth (30). The tooth (30) has front and back walls that are joined together by left and right sidewalls. The channel extends (34) through the rectangular-like structure of the tooth. As discussed above, the top surface of the tooth also has a top opening (36) so that when the tooth base is affixed to the base member of the main body member, a bottom opening (38) is present that allows the composition to be dispensed. The composition can flow through the tooth (30) and be dispensed onto the scalp. The composition flows through the teeth (30) onto the scalp. The teeth (30) also can be used to massage the composition into the scalp when the applicator (10) is run along the scalp. The top surface of the tooth (30) can have any suitable geometry. For example, the top portion of the tooth (30) can have a planar, curved, rounded, sloped, or other type of surface. Also, the top surface can have a rectangular, square, oval, or other shaped cross-section.

Figure 7:
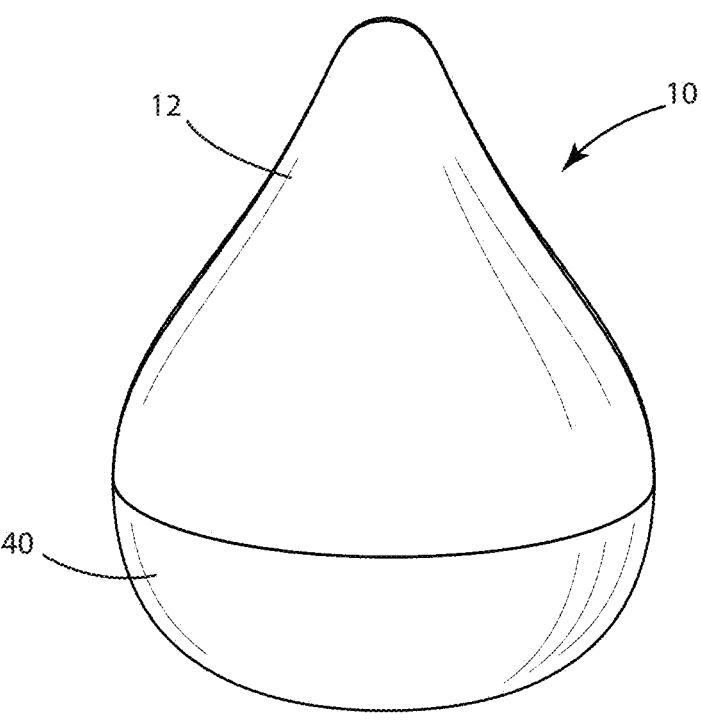
FIG. 7 is a perspective view of one embodiment of the scalp treatment applicator of the present invention showing the lower cap fastened to the upper handle.
Figure 8:
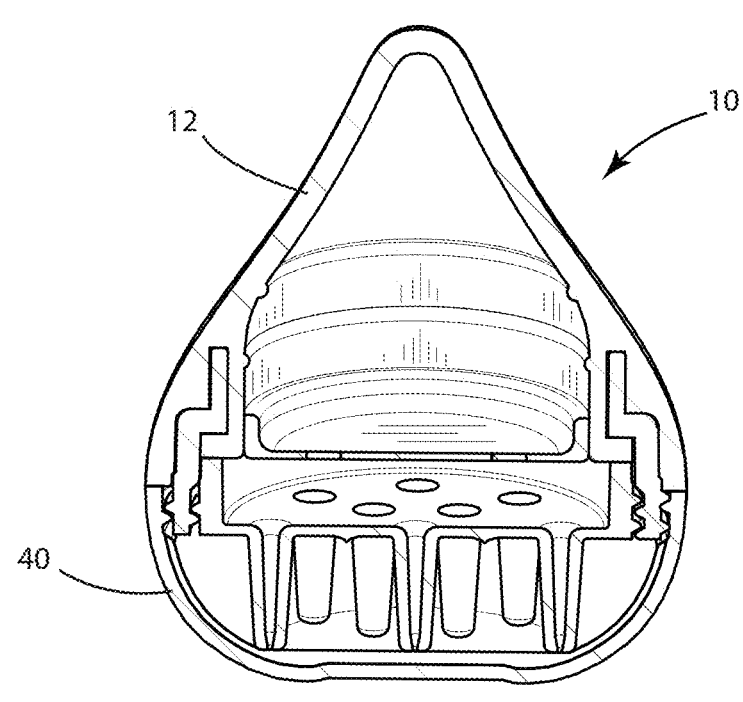
FIG. 8 is cross-sectional view of the scalp treatment applicator shown in FIG. 7.

As shown in FIGS. 7 and 8, when the applicator device (10) is not being used, the lower cap (40) can be screwed onto the outer surface of the head member (22). In this way, the applicator (10) is sealed. The applicator (10) can be carried and stored easily. When the applicator device (10) is closed with the lower cap (40), the device has an aesthetically-pleasing tear-shaped appearance.

The present invention also encompasses methods of applying a scalp treatment composition to the scalp of a user. In one preferred embodiment, the method comprises the following steps: i) providing an applicator as described above. The applicator comprises: a) an upper handle having upper and lower portions, the upper and lower portions defining a hollow cavity, the lower portion being adapted for receiving a main body member; b) a main body member, the main body member being attached to the upper handle, the main body member comprising a head member, insert member, and base member, the insert member being disposed between the head member and base member, and the base member being removably coupled to the head member; c) multiple teeth extending downwardly from the base member, at least one tooth having a neck containing a channel that extends from a top opening, through the neck of the tooth, and terminates at a bottom opening of the tooth, from which the composition is dispensed; and d) a removable lower cap for enclosing the main body member, the lower cap being removably fastened to the upper main body member; ii) loading the applicator with a scalp treatment composition; and iii) dispensing the composition onto the scalp by contacting the scalp with the multiple teeth extending downwardly from the base member.

The scalp treatment applicator of the present invention can be used for applying any hair and scalp treatment compositions including, but not limited to, hair oils and serums, medications, shampoos, conditioners, hair coloring formulations, hair bleach, and hair gels.

The scalp treatment applicator of the present invention provides many benefits. For example, the applicator of this invention can uniformly apply the scalp treatment composition so that globs and clumps do not form in the hair. The scalp treatment applicator further has a unique tear-shaped design and is consumer-friendly. The scalp treatment composition is dispensed onto the scalp by the user squeezing the upper handle of the applicator. The user can control the amount of scalp treatment composition that is dispensed by adjusting the pressure applied to the upper handle. The scalp treatment applicator of the present invention has many other advantageous features.

It should be understood the terms, "first", "second", "top", "bottom", "above", "below", "upper", "lower", "intermediate", "head' "base" "upwardly", "downwardly", "right", "left", and the like are arbitrary terms used to refer to one position of an element based on one perspective and should not be construed as limiting the scope of the invention.

It should be understood that the assemblies, devices, constructions, materials, methods, and the like described and illustrated herein represent only some embodiments of the invention. It is appreciated by those skilled in the art that various changes and additions can be made to the assemblies, devices, construction, materials, methods, and the like without departing from the spirit and scope of this invention. It is intended that all such embodiments be covered by the appended claims.

We claim:

1. A scalp treatment applicator for applying a scalp treatment composition to a scalp of a user, the applicator comprising:
    an upper tapered handle having upper and lower portions, the upper and lower portions defining a hollow cavity, the lower portion being adapted for receiving a main body member;
    a main body member, the main body member comprising a head member, insert member, and base member, wherein the insert member is removably fitted into the head member, the insert member having an upper surface and a lower surface and wherein a tab extends downwardly from the lower surface and wherein the head member containing the insert member is fastened to the upper handle and wherein the base member has outer screw threads and the head member has inner screw threads so that the base member is removably screwed onto the head member;
    multiple teeth extending downwardly from the base member, at least one tooth having a neck containing a channel that extends from a top opening, through the neck of the tooth, and terminates at a bottom opening of the tooth, from which the composition is dispensed; and
    a removable lower rounded cap for enclosing the main body member, the lower rounded cap being removably fastened to the upper handle such that the applicator has a tear-shaped structure.

2. The scalp treatment applicator of claim 1, wherein the upper handle is made of a plastic material so that the handle can be squeezed to dispense the scalp treatment composition.

3. The scalp treatment application of claim 1, wherein the upper handle is conical shaped.

4. The scalp treatment applicator of claim 1, wherein the head member is integrally molded to the upper handle.

5. The scalp treatment applicator of claim 1, wherein the head member is snap-fitted to the upper handle.

6. The scalp treatment applicator of claim 1, wherein the head member has a threaded inner surface and the base member has a threaded outer surface so that the base member can be screwed into the head member.

7. The scalp treatment applicator of claim 1, wherein the insert divider contains divider members that define slits for dispensing the scalp treatment composition.

8. The scalp treatment applicator of claim 1, wherein the teeth extending downwardly from the base member are rectangular shaped.

* * * * *